United States Patent
Winn

(10) Patent No.: US 10,939,985 B2
(45) Date of Patent: Mar. 9, 2021

(54) STERILE LUBRICATED BREAST IMPLANT

(71) Applicant: R. Alastair Winn, Santa Barbara, CA (US)

(72) Inventor: R. Alastair Winn, Santa Barbara, CA (US)

( * ) Notice: Subject to any disclaimer, the term of this patent is extended or adjusted under 35 U.S.C. 154(b) by 189 days.

(21) Appl. No.: 16/029,411

(22) Filed: Jul. 6, 2018

(65) Prior Publication Data

US 2019/0117365 A1 Apr. 25, 2019

Related U.S. Application Data

(60) Provisional application No. 62/531,731, filed on Jul. 12, 2017.

(51) Int. Cl.
 *A61F 2/00* (2006.01)
 *A61F 2/52* (2006.01)
 *A61B 17/34* (2006.01)
 *A61F 2/12* (2006.01)
 *A61B 17/00* (2006.01)

(52) U.S. Cl.
 CPC ........ *A61F 2/0095* (2013.01); *A61B 17/3468* (2013.01); *A61F 2/52* (2013.01); *A61B 2017/00796* (2013.01); *A61B 2017/00845* (2013.01); *A61B 2017/00907* (2013.01); *A61B 2017/00942* (2013.01); *A61F 2/12* (2013.01)

(58) Field of Classification Search
 CPC .................................. A61B 17/34; A61F 2/12
 See application file for complete search history.

(56) References Cited

U.S. PATENT DOCUMENTS

| | | | |
|---|---|---|---|
| 4,610,690 A * | 9/1986 | Tiffany | A61F 2/12 623/8 |
| 7,935,089 B2 | 5/2011 | Tsao | |
| 8,211,173 B2 | 7/2012 | Keller et al. | |
| 9,277,905 B2 | 3/2016 | Cully et al. | |
| 9,641,758 B2 | 5/2017 | Watanabe | |
| 2003/0203991 A1* | 10/2003 | Schottman | C09D 201/00 523/334 |
| 2007/0185575 A1* | 8/2007 | Purkait | A61F 2/12 623/8 |
| 2014/0148901 A1 | 5/2014 | Anderson et al. | |
| 2014/0228951 A1 | 8/2014 | Zochowski | |
| 2015/0032208 A1 | 1/2015 | Preissman | |
| 2015/0126812 A1 | 5/2015 | Anderson | |
| 2015/0297339 A1 | 10/2015 | Placik et al. | |
| 2016/0038275 A1 | 2/2016 | Preissman | |
| 2016/0074559 A1 | 3/2016 | Rosenblatt et al. | |
| 2016/0095696 A1 | 4/2016 | Anton | |
| 2016/0095697 A1 | 4/2016 | Anderson | |
| 2016/0270894 A1* | 9/2016 | Labrecque | A61F 2/0063 |
| 2018/0116779 A1* | 5/2018 | Marx | A61F 2/12 |

OTHER PUBLICATIONS

Internationals Search Report and Written Opinion of the International Searching Authority for PCT/US2018/041169 dated Sep. 10, 2018.

* cited by examiner

*Primary Examiner* — Yashita Sharma

(74) *Attorney, Agent, or Firm* — Fitzgerald IP Law; John K. Fitzgerald, Esq.

(57) ABSTRACT

A method for coating a sterile breast prosthesis packaged within a sterile blister package with a lubricious material while maintaining the sterility of the breast prosthesis is described.

6 Claims, 1 Drawing Sheet

STERILE LUBRICATED BREAST IMPLANT

CROSS-REFERENCE TO RELATED APPLICATIONS

This application claims priority to the earlier filed U.S. Provisional Application No. 62/531,731, filed on Jul. 12, 2017, entitled "Sterile Lubricated Breast Implant" which is incorporated by reference herein in its entirety.

BACKGROUND

This invention is directed to a delivery apparatus and method for inserting a breast prosthesis in the body of a patient.

Implantable breast prostheses have been in worldwide use for a number of years. One problem with the insertion of implantable breast prostheses is that the implantable prostheses are often provided in a filled condition and must be inserted into a surgical pocket. As a result, traditional surgical approaches have required the use of relatively large incisions.

Insertion of an implantable breast prostheses typically requires substantial manual manipulation by the surgeon of the implant in order to insert it into the surgical pocket. Recently, a number of insertion aides have been developed to reduce the size of the incision needed and to ease the actual implantation of the implantable breast prosthesis. One such aide is a flexible funnel shaped device having a large proximal opening into which an implantable breast prosthesis may be placed, and a smaller distal opening which may be placed into an appropriately sized incision in the patient. The implantable breast prosthesis is then inserted through the incision by squeezing the funnel shaped device to forcibly express the implantable breast prosthesis through the distal opening past the incision site and into the surgical pocket.

It has been observed that the use of a flexible funnel shaped device may be disadvantageous for a number of reasons. First, the inner walls of the flexible funnel shaped device may have a relatively high coefficient of friction, resulting in the exterior of the implantable breast prosthesis "sticking" to the inner wall of the funnel, which may damage the prosthesis, funnel, or both, and requiring a high level of compression to insert the prosthesis in to the surgical pocket.

Various methods have been used to lubricate a breast prosthesis prior to implantation in a person. Typically, these methods require the breast prosthesis to be removed from its sterile package and then put into contact with a lubricant. For example, in one prior method, the breast prosthesis is removed from its sterile blister package and then placed in a container of lubricous liquid. Such a method is disadvantageous because the coating of the prosthesis occurs in an environment where contamination of the coating liquid and the prosthesis may occur.

What has been need, and heretofore unavailable, is a method which provides for lubrication of the implantable breast prosthesis in a sterile environment, ensuring that the coated prosthesis remains sterile during the coating procedure. The present invention satisfies these and other needs.

SUMMARY OF THE INVENTION

In its most general aspect, the invention includes a system and method for coating a breast prosthesis with a sterile lubricious material in a surgical suite in a manner that conserves the sterility of the prosthesis in its packaging. In this manner, the sterile coated prosthesis may then be implanted through a surgical incision. The sterile, coated, breast prosthesis is placed into a flexible funnel shaped body.

In another aspect, the funnel shaped body includes an inner wall forming a lumen through which the breast prosthesis is pushed to implant the breast prosthesis into the patient. In such an aspect, the inner wall may be coated with a lubricious material. The lubricious material may be applied as a coating onto the inner wall of the funnel shaped body, or the inner wall may be modified chemically to bond to a lubricious material deposited or formed on the surface of the inner wall.

In yet another aspect, the present invention includes a system for use in the implantation of a breast prosthesis into a patient through a surgical incision, comprising: a system for use in the implantation of a breast prosthesis into a patient through a surgical incision, comprising: a sterile breast prosthesis contained within a sterile blister package; a sterile injector containing a sterile bio-compatible and bio-absorbable lubricious material; a flexible funnel shaped body having a proximal end having a first opening having a diameter sized to receive a breast prosthesis, the funnel shaped body having a distal end having a second opening having a diameter that is smaller than the first opening; and, wherein the sterile breast prosthesis is coated with the sterile bio-compatible and bio-absorbable lubricious material while contained in the sterile blister package prior to being placed with the flexible funnel shaped body.

In still another aspect, the flexible funnel shaped body has an inner wall, and further comprising a lubricant applied to the inner wall. In another alternative aspect, the flexible funnel shaped body has an inner wall, the inner wall including a layer of lubricious material configured to contact a breast prosthesis inserted into the funnel shaped body.

In still another aspect, the present invention includes a method of coating a breast prosthesis with a sterile lubricious material prior to implanting the breast prosthesis into a patient, comprising: injecting a sterile lubricious material into a sterile package containing a sterile breast prosthesis; and shaking the sterile package and sterile breast prosthesis to coat a surface of the sterile breast prosthesis with the sterile lubricious material. In one alternative aspect, the sterile lubricious material is hyaluronic acid. In still another aspect, the sterile lubricious material is 2% hyaluronic acid.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As will be described hereinafter in greater detail, the various embodiments of the present invention relate to an apparatus and method for facilitating insertion of an implantable breast prosthesis. For purposes of explanation, specific nomenclature is set forth to provide a thorough understanding of the present invention. Description of specific applications and methods are provided only as examples. Various modifications to the embodiments will be readily apparent to those skilled in the art and the general principles defined herein may be applied to other embodiments and applications without departing from the spirit and scope of the invention. Thus the present invention is not intended to be limited to the embodiments shown, but is to be accorded the widest scope consistent with the principles and steps disclosed herein.

In describing the various figures herein, the same reference numbers are used throughout to describe the same element that appears in more than one embodiment of the present invention. Detailed descriptions of various elements that appear in more than one embodiment is not repeated in the descriptions of following figures, even though such element is labeled with the same reference number.

Figure 1:
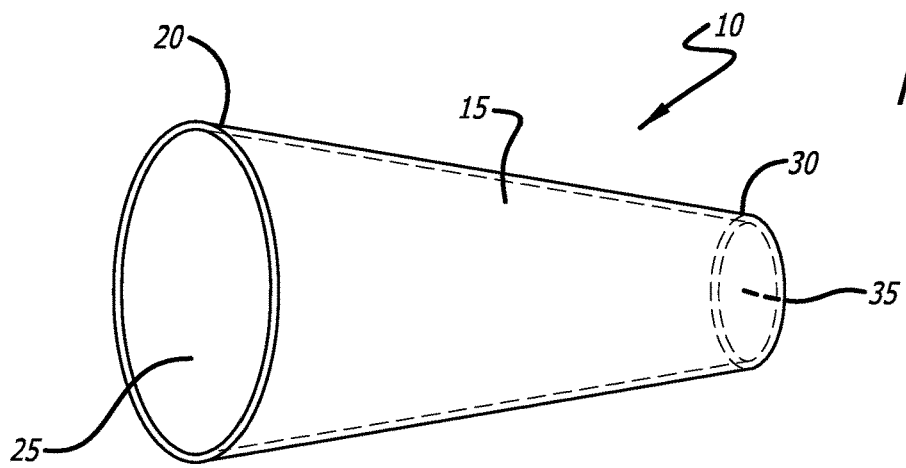
FIG. 1 is a side perspective view of one embodiment of the present invention.

FIG. 1 illustrates one embodiment of a breast implantation funnel 10 in accordance with various principles of the present invention. The funnel 10 has a flexible body 15 having a proximal end 20. Proximal end 20 has an opening 25 that is sized to receive a breast prosthesis to be implanted into a patient. Funnel 10 also has a distal end 30 having an opening 35.

Typically, the flexible body 15 of the funnel 10 is comprised of a flexible and transparent material. Such materials may include medical grade flexible plastic materials such as PVC mixed with a suitable plasticizer, ethylene vinyl acetate or a polyolefin, such as polypropylene, or a medical grade silicone elastomer. Such materials are flexible, strong and are capable of slightly stretching without rupture. It is also useful if the material used to form the body of the funnel is transparent or translucent so that the orientation of the breast prosthesis may be directly observed as it is being implanted.

Figure 2:
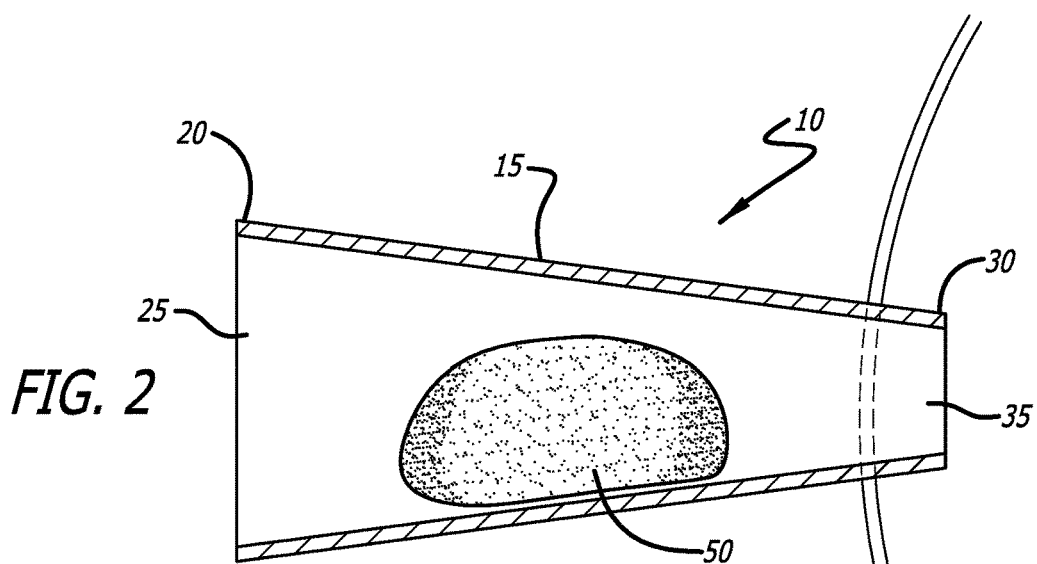
FIG. 2 is cut away side perspective view of the embodiment of FIG. 1 depicted as inserted through a surgical incision and into a cavity formed within a chest area of a patient.

FIG. 2 illustrates the use of the funnel 10 to assist the implantation of a breast prosthesis 50. As shown, breast prosthesis 50 is inserted into the opening 25 disposed at the proximal end 20 of the funnel. The prosthesis 50 is typically manipulated through the body 15 of the funnel towards the opening 35 disposed in the distal end 30 of the funnel. Because of the slope of the funnel which results in the diameter of opening 35 being smaller than that of opening 25, there is a point where the prosthesis becomes lodged within the funnel. At that point, the surgeon may take hold of the funnel in the proximity of the proximal end 20 and begin the squeeze the outer wall of the body 15 to impart pressure on the prosthesis in a distal direction, ultimately causing the prosthesis to be expelled through opening 35 in the distal end 30 of the funnel into a cavity formed within the patient's chest.

In another embodiment of the present invention, a lubricating substance may be coated on an inner wall of the funnel body 15. The coating may, for example, consist of an ionic lubricant, including hydrophilic lubricants as manufactured by, or similar to, those manufactured by Advanced Biomaterials, AST Products, Biocoat, Coatingstogo, DSM, Harland MedicalSystems, Surface Solutions Group or PolyBioMed. Other conventional commercially available surgical lubricants can also be used, such as Surgilube™, or gels, such as, for example, Aquasonic™ and the like that may or may not contain common antibiotics such as bacitracin or other antimicrobial (antibacterial, antiviral, antifungal) agents.

In yet another embodiment, the surface of the inner wall of the funnel body may be by forming a hydrophilic coating on the surface of the inner wall. As is known in the art, surfaces have been rendered hydrophilic by such methods as high energy radiation in situ polymerization processes, by direct chemical bonding or by forming interpolymer networks. The radiation process can render a very stable hydrophilic surface, but suffers from unreliable results and can produce radiation damage to the substrate. Formation of interpolymer networks also produces hydrophilic surfaces but in turbulent flow or extended soaking, the interpolymer networks often break down and the hydrophilic portion can be washed away rendering the substrate surface defective.

Other methods described in the art use a polyurethane coating agent to adhere poly-N-vinyl pyrollidone (PVP) to various substrates, thus producing an article having a hydrophilic coating of low coefficient friction. Extensive studies indicate, however, that in turbulent flow or upon extended soaking in aqueous media, the hydrophilic coating can be leeched off, thus rendering the article insufficiently hydrophilic.

Another method for creating a hydrophilic coating on an article, such as, for example, the funnel-shaped body described above coating the inner wall of the funnel-shaped body with a polyisocyanate and a hydrophilic copolymer having pendant groups which react with the isocyanates. The polyisocyanate and the hydrophilic copolymer produce a covalent graft or bond between the hydrophilic coupling agent and the hydrophilic copolymer.

In one such embodiment, the inner wall of the funnel-shaped body may be is exposed to a polyisocyanate in a solvent solution by dripping, spraying or the like and then evaporating the solvent preferably by air drying. This step forms a coating with unreacted isocyanate groups on the surface of the substrate. A copolymer having an average of at least two active hydrogen atom sites per molecule is then applied to the surface of the substrate and reacts with the unreacted isocyanate groups to produce a covalently bound matrix, thus forming a stable hydrophilic coating.

In another embodiment, the hydrophilic copolymer and polyisocyanate can be applied to the inner wall of the funnel-shaped body from solvent simultaneously. Thus the polyisocyanate can crosslink the copolymer to the inner wall of the funnel-shaped body and to itself. Extended soaking to form better interpenetrating polymer networks between the inner wall of the funnel-shaped body and the hydrophilic network may improve bonding of the hydrophilic material to the inner wall of the funnel-shaped body.

When the funnel-shaped body is formed of low surface energy materials (less that 32 dynes/cm$^2$, those materials will not bond well with polyisocyanate systems. Bonding to such low surface energy materials can be improved by solvent aided interpolymer networks or by modifying the inner wall of the funnel-shapted body with radiation, oxidizing agents such as ozonoloysis or coupling agents such as gamma-amino propyl triethoxy silane.

A more detailed explanation of exemplary processes and materials that may be used to form a lubricious layer of low friction hydrophilic matter on the inner wall of the funnel-shaped body is described by Winn in U.S. Pat. No. 4,373,009, the entirety of which is hereby incorporated herein.

Figure 3:
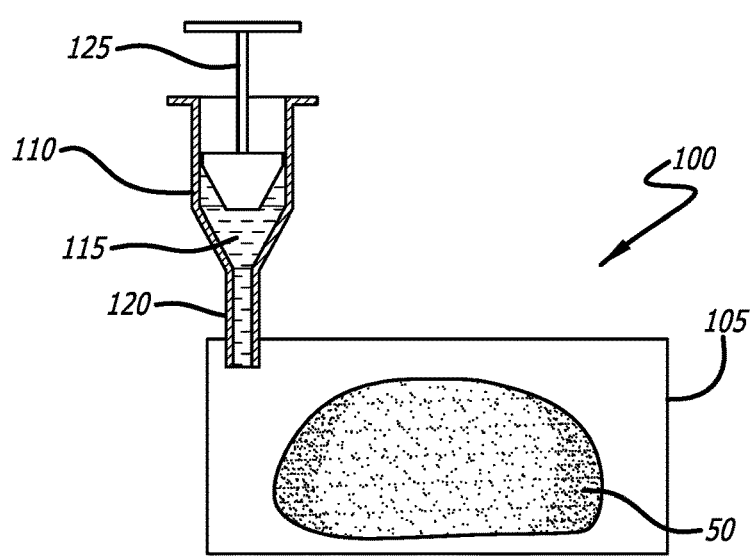
FIG. 3 is a side view in cross-section of an embodiment of the present invention wherein a sterile lubricious material is injected into the sterile interior of packaged breast prosthesis.

FIG. 3 depicts another embodiment 100 of the present invention wherein the breast prosthesis 50 is sterilely packaged within a blister package 105, as is common in the art. In this embodiment, a sterilized injector 110 or other suitable device may be used to inject a sterile lubricious material 115, such as, for example, but not limited to, a 2% hyaluronic acid, through a suitable needle 120 or other device configured to penetrate the blister package. As shown, pressing a plunger 125 of the injector 110 forces the lubricious material 115 through needle 120 into the interior of the blister package, while maintaining sterility of the interior of the blister package and breast prosthesis.

After the lubricious material is injected into the interior of the blister package, the blister package may be shaken to coat the breast prosthesis. The coated breast prosthesis is then removed from the blister package, and placed into a solid or woven plastic funnel as described above, and them forced through a device such as the funnel-shaped body described above to implant the breast prosthesis into the chest of a patient. As well known in the art, where the lubricious material is, for example, a bio-compatible and bio-absorbent material such as 2% hyaluronic acid, the lubricious material does not need to be removed at the end of the implantation procedure because it will reabsorb into the patient's body. Suitable aqueous solutions of hyaluronic acid include solutions from 0.1% to 10.0% hyaluronic acid solutions, and preferably between 1.0%-3.0%, more preferably 1.5%-2.5%, and also more preferably approximately 2.0% hyaluronic acid.

While particular embodiments of the present invention have been described, it is understood that various different modifications within the scope and spirit of the invention are possible. The invention is limited only by the scope of the appended claims.

I claim:

1. A system for use in the implantation of a breast prosthesis into a patient through a surgical incision, comprising:
   a sterile breast prosthesis contained within a sterile blister package;
   a sterile injector containing a sterile bio-compatible and bio-absorbable lubricious material;
   a sterile flexible funnel shaped body having a proximal end having a first opening having a diameter sized to receive a breast prosthesis, the funnel shaped body having a distal end having a second opening having a diameter that is smaller than the first opening, the flexible funnel shaped body having an inner wall;
   a layer of lubricious material bonded to the inner wall of the flexible funnel shaped body prior to sterilization of the flexible funnel shaped body; and,
   wherein the sterile breast prosthesis is coated with the sterile bio-compatible and bio-absorbable lubricious material while contained in the sterile blister package by using the sterile injector to inject the sterile bio-compatible and bio-absorbable lubricious material into the sterile blister package prior to the sterile breast prosthesis being removed from the sterile blister package and being placed into the flexible funnel shaped body.

2. The system of claim 1, wherein the lubricious material is chemically bonded to the inner wall.

3. The system of claim 1, wherein the lubricious material is ionically bonded to the inner wall.

4. The system of claim 1, where the lubricious material bonded to the inner wall is a component of an interpolymer network.

5. The system of claim 1, wherein lubricious material bonded is a polyisocyanate and hydrophilic copolymer blend.

6. The system of claim 2, wherein the chemical bond is a covalent bond.

* * * * *